(12) United States Patent
Drahos et al.

(10) Patent No.: US 6,194,193 B1
(45) Date of Patent: Feb. 27, 2001

(54) NUTRIENT PLANT FORMULATION WITH MICROBIAL STRAINS

(76) Inventors: David J. Drahos, 6014 Scotford Ct., Roanoke, VA (US) 24018; Donald J. Miller, 712 Lucas Dr., Blacksburg, VA (US) 24060

( * ) Notice: Subject to any disclaimer, the term of this patent is extended or adjusted under 35 U.S.C. 154(b) by 0 days.

(21) Appl. No.: 09/209,767

(22) Filed: Dec. 11, 1998

(51) Int. Cl.$^7$ ........................................................ C12N 1/20
(52) U.S. Cl. .................... 435/252.4; 47/58.1; 435/252.5; 435/431; 504/117; 504/118
(58) Field of Search ................................ 435/431, 252.4, 435/252.5; 47/58.1; 504/117, 118

(56) References Cited

U.S. PATENT DOCUMENTS

| | | | |
|---|---|---|---|
| 4,061,488 | * 12/1977 | Mann | 504/117 |
| 5,061,490 | * 10/1991 | Paau et al. | 504/117 |

OTHER PUBLICATIONS

FEMS Microbiology Ecology 22, by Michael Lebuhn et al., "Production of auxin and other indolic and phenolic compounds by *Paenibacillus polymyxa* strains isolated from different proximity to plant roots", 1997, pp. 325–334.

Soil Biol. Biochem. vol. 23, No. 4, by Emily L. Selvadurai et al., "Production of Indole–3–Acetic Acid Analogues by Strains of *Bacillus Cereus* in Relation to Their Influence on Seedling Development", pp. 401–403.

Biol Fertil Soils by Michael Lebuhn et al., "Effects of drying/rewetting stress on microbial auxin production and L–tryptophan catabolism in soils", 1994, pp. 18:302–310.

Planta by Göran Sandberg, "Biosynthesis and metabolism of indole–3–ethanol and indole–3–acetic acid by *Pinus sylvestris* L. needles", 1984, pp. 161:398–403.

Z. Pflanzenernähr.Bodenk., by P. Martin et al., "$N_2$–fixing bacteria in the rhizophere: Quantification and hormonal effects on root development", 1989, pp. 152.237–245.

Z. Pflanzenernähr.Bodenk., by Martin Müller et al., "Hormonal interactions in the rhizosphere of maize (*Zea mays* L.) and their effects on plant development", 1989, pp. 152, 247–254.

Agricultural Research, Science and Education Administration, U.S. Department of Agriculture, Pullman, WA, by R. James Cook, "Fusarium Foot Rot of Wheat and Its Control in the Pacific Northwest", 1980, pp. 1061–1066.

Plant Pathology, by R.J. Cook et al., Virulence of *Gaeumannomyces graminis* var. *tritici* from fields under short–term and long–term wheat cultivation in the Pacific Northwest, U.S.A., (1982) pp. 201–207.

Science, by Milton N. Schroth et al., "Disease–Suppressive Soil and Root Colonizing Bacteria", Jun. 1982, pp. 1376–1381.

Advances in Agronomy, Volume 62, by Muhammad Arshad et al., "Plant Growth–Regulating Substances in the Rhizosphere: Microbial Production and Functions", 1998, pp. 45–151.

College of Natural Resources, Agricultural Experiment Station, Department of Plant Pathology, Berkeley, California 94720, by M.N. Schroth, et al., "Bacteria as Biocontrol Agents of Plant Disease", pp. 362–369.

Current Microbiology Vol. 37, by Laura A. Silo–Suh et al., Target Range of Zwittermicin A, an Aminopolyol Antibiotic from *Bacillus cereus*, 1998, pp. 6–11.

FEMS Microbiology Ecology, by Preben Nielsen et al., "Multi–target and medium–independent fungal antagonism by hydrolytic enzymes in *Paenibacillus polymyxa* and *Bacillus pumilus* strains from barley rhizosphere", 1997, pp. 183–192.

Applied and Environmental Microbiology, by A. Gaballa et al., "Trehalose Induces Antagonism towards *Pythium debaryanum* in *Pseudomonas fluorescens* ATCC 17400†", Nov. 1997, pp. 4340–4345.

Plant and Soil, by Lucy Seldin et al., "Bacillus nirtogen fixers from Brazilian soils", 1983, pp. 243–255.

International Journal of Systematic Bacteriology, by L. Seldin et al., "*Bacillus azotofixans* sp. nov., a Nitrogen–Fixing Species from Brazilian Soils and Grass Roots", Oct. 1984, pp. 451–456.

Applied and Environmental Microbiology, by Kenji Sakai et al., Purification and Characterization of Three Thermostable Endochitinases of a Noble *Bacillus* Strain, MH–1, Isolated from Chitin–Containing Compost, Sep. 1998, pp. 3397–3402.

Applied and Environmental Microbiology, by M.T. Brandl et al., "Contribution of Indole–3–Acetic Acid Production to the Epiphytic Fitness of Erwinia herbicola", Sep. 1998, pp. 3256–3263.

* cited by examiner

*Primary Examiner*—Leon B. Lankford, Jr.
(74) *Attorney, Agent, or Firm*—Owen D. Marjama; Mishrilal Jain

(57) ABSTRACT

A liquid and dry formulation suitable for use in enhancing plant growth which includes a plurality of Bacillus and Paenibacillus strains at least one of which function to produce phytohormones in a non-toxic form. The formulation also includes a phytohormone component and a phytohormone precursor to potentiate roots for colonization by the inoculated strains, as well as a low level blend of nutrients and micronutrients for optimal plant development.

15 Claims, 9 Drawing Sheets

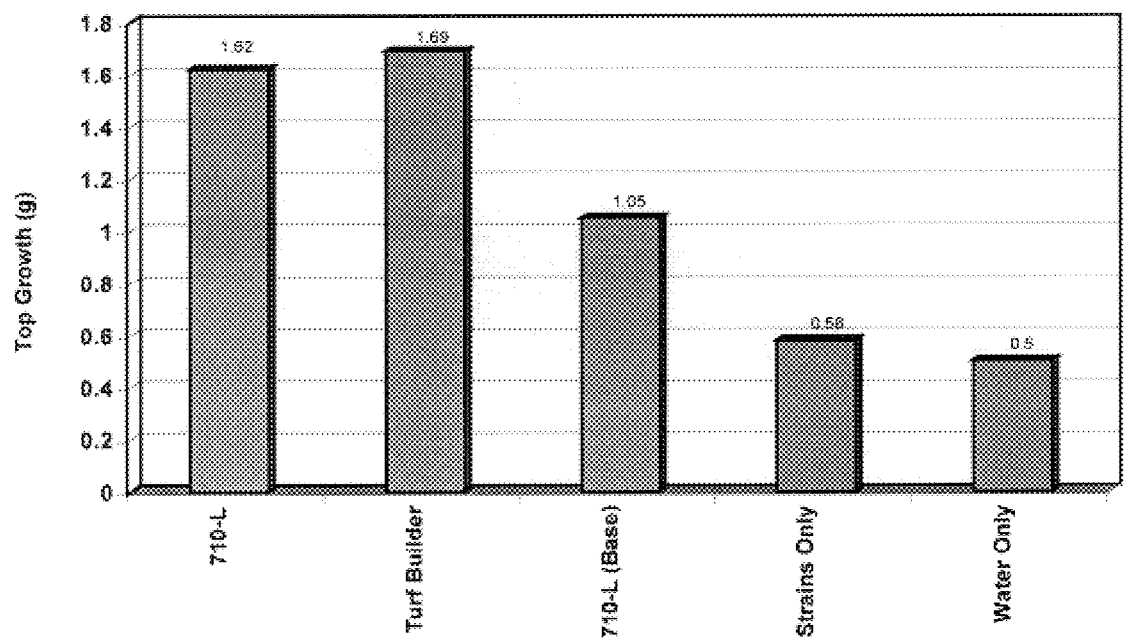
Fig. 1 Turf Growth Chamber Trials 710-L (without IBA/Trp)
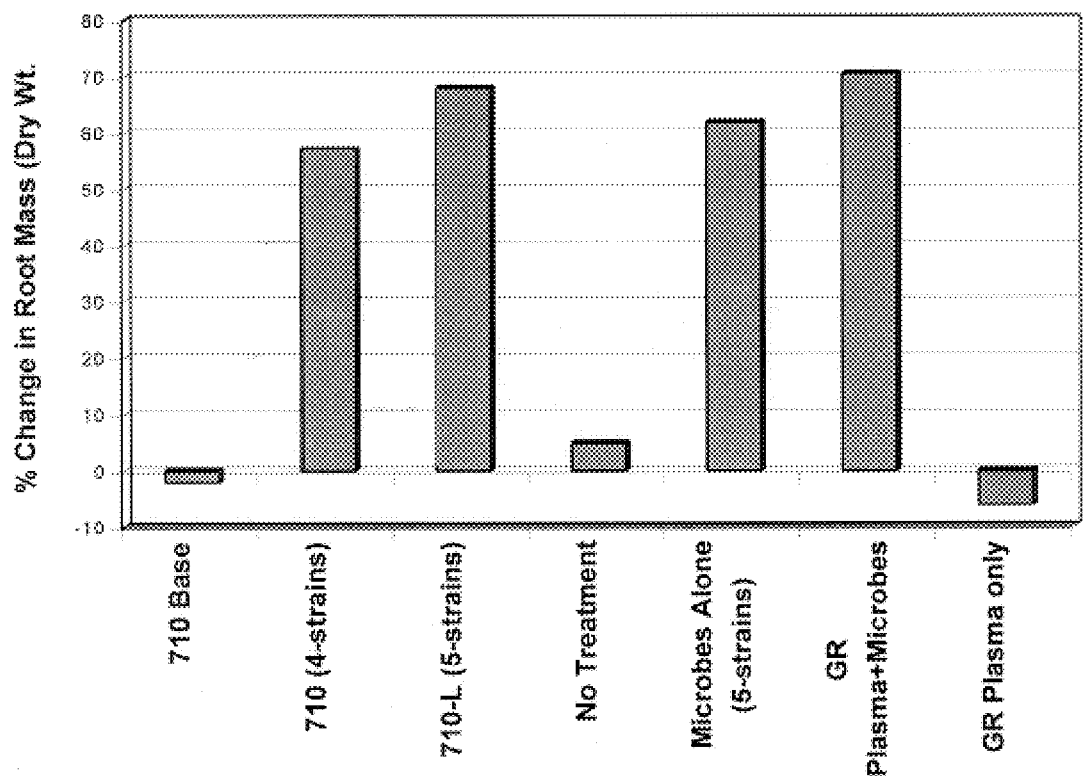
Fig. 2. Turf Field Trials: Hollyfield Golf Course (8-Week Treatment)

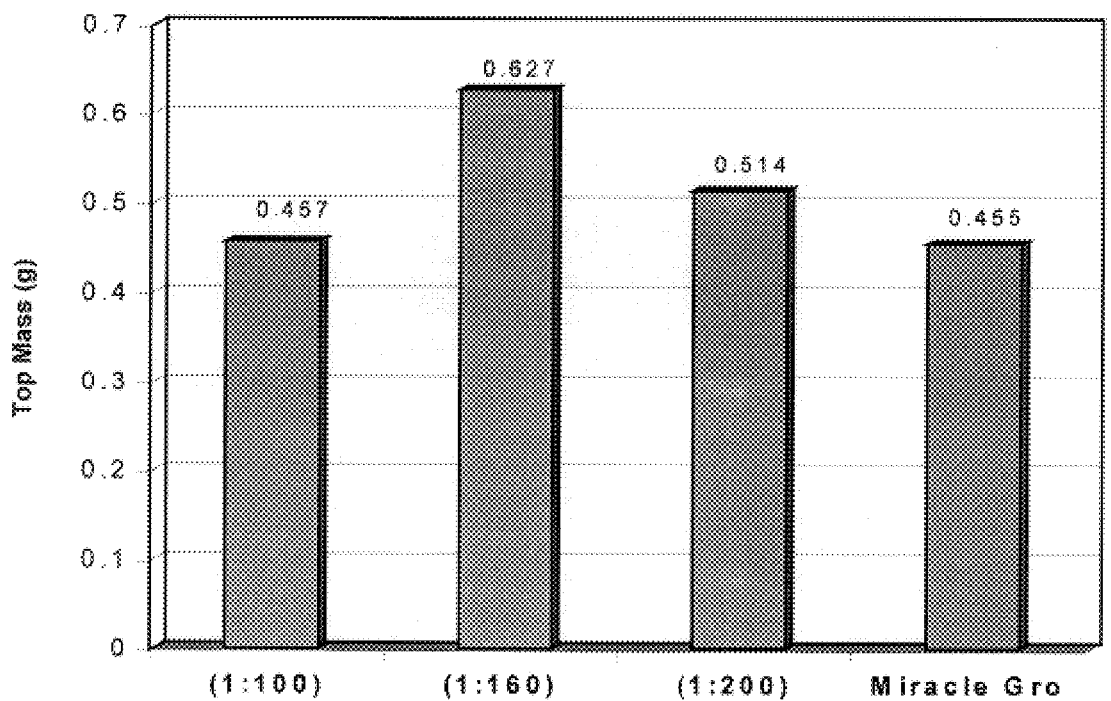
Fig. 3a. Greenhouse Test: Tomato Top Mass
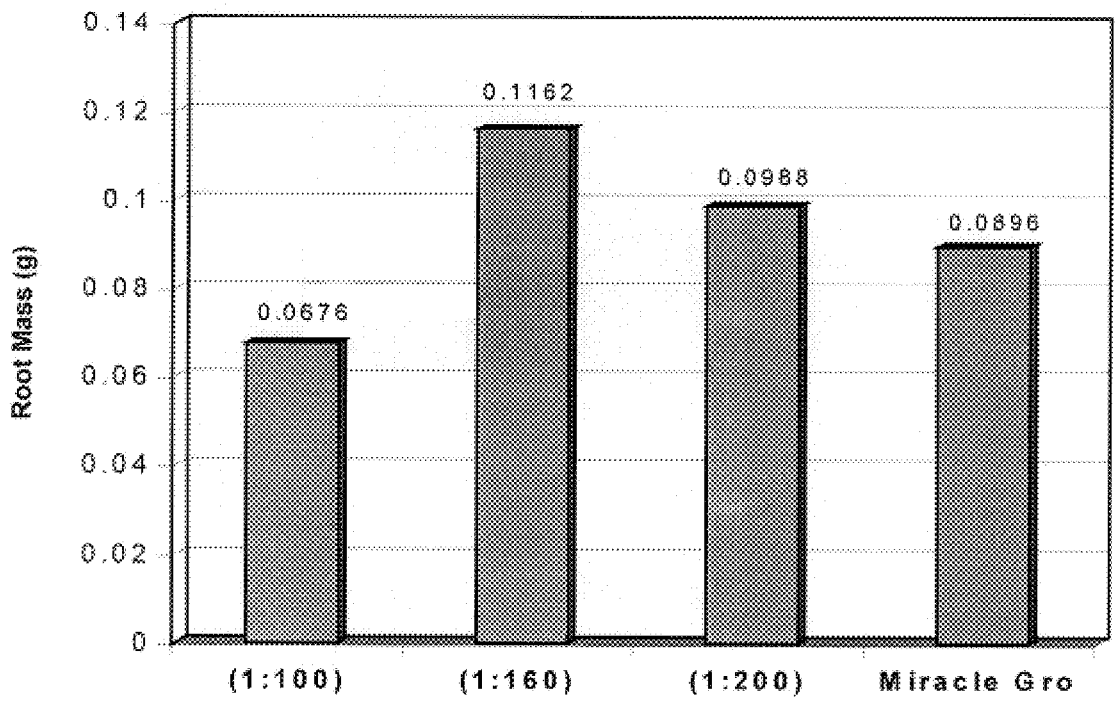
Fig. 3b. Greenhouse Test: Tomato Root Mass

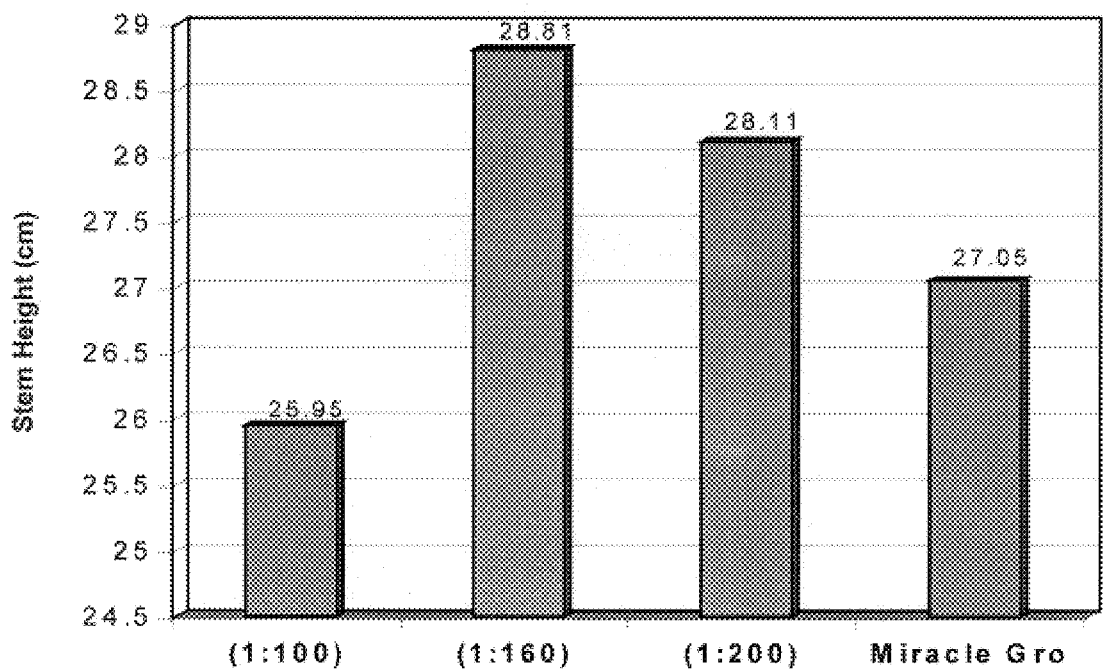
Fig. 3c. Greenhouse Test: Tomato Stem Height
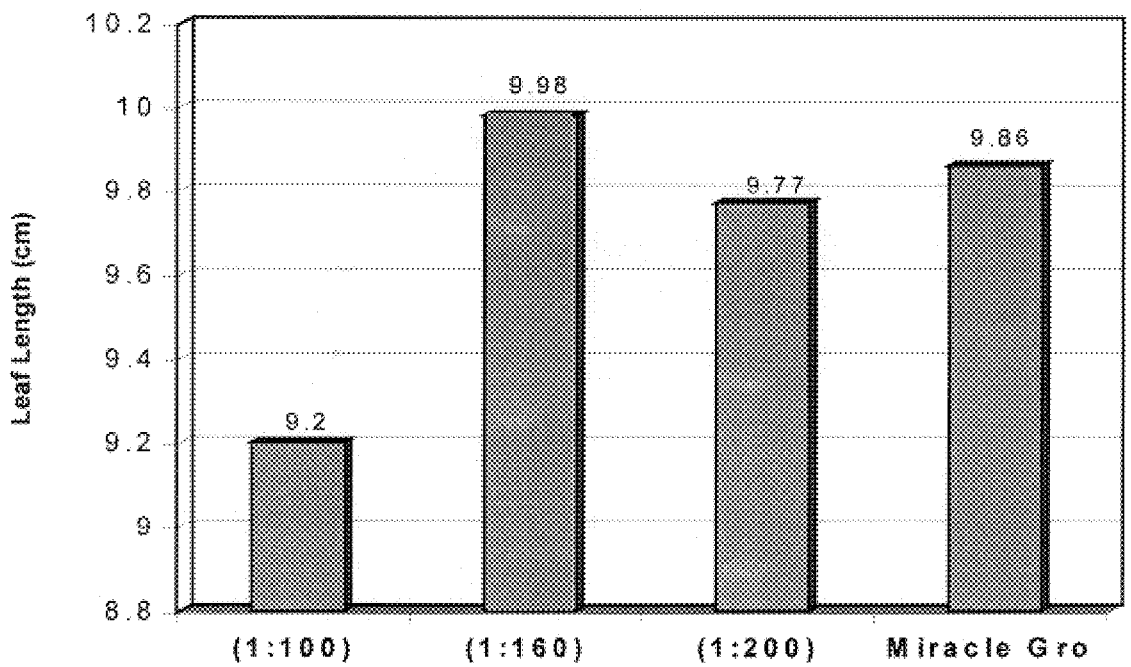
Fig. 3d. Greenhouse Test: Leaf Length

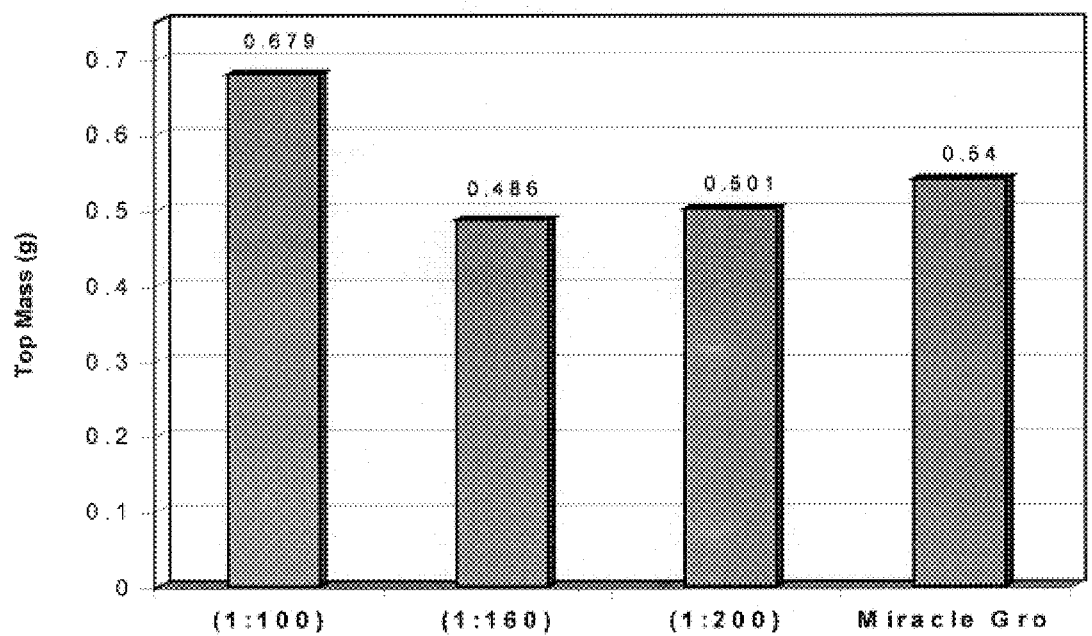
Fig. 4a. Greenhouse Test: Tomato Top Mass
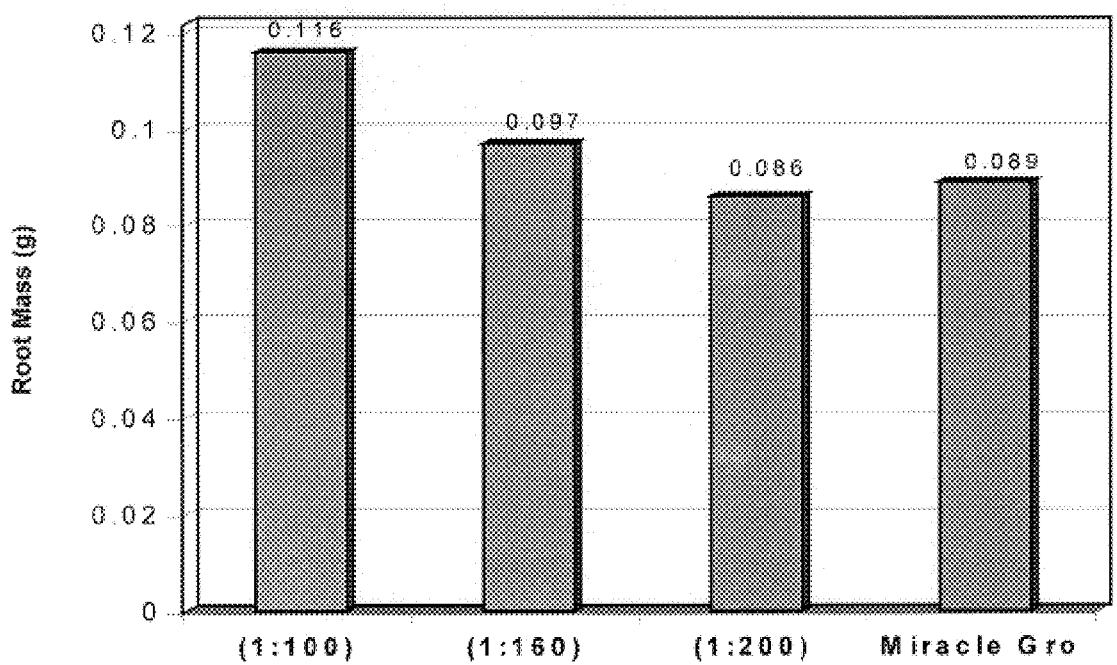
Fig. 4b. Greenhouse Test: Tomato Root Mass

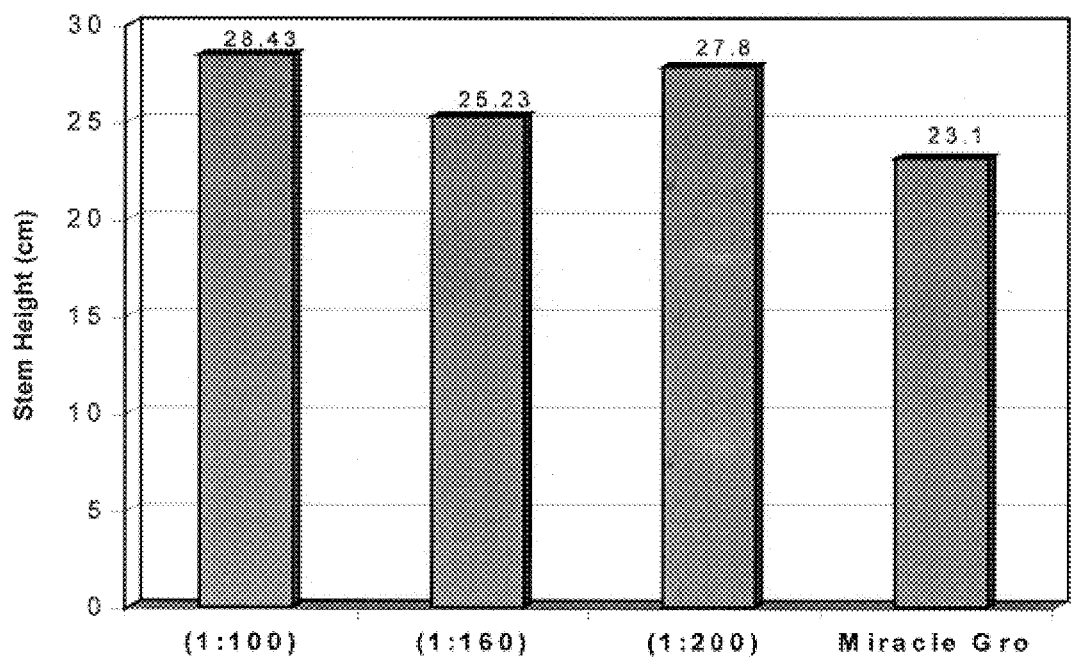
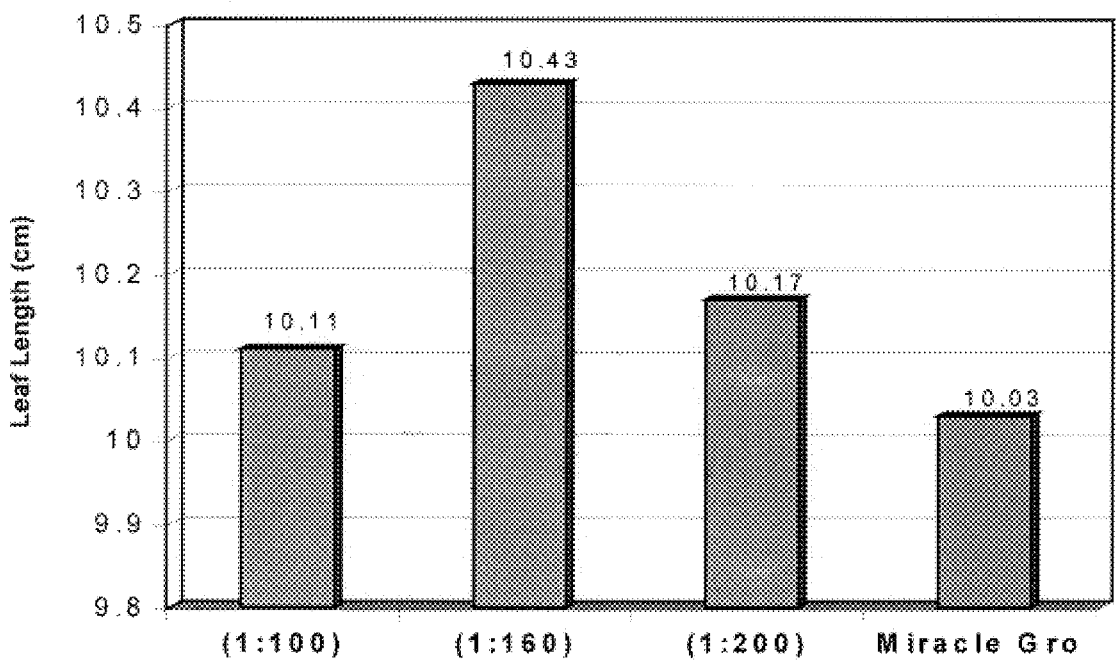

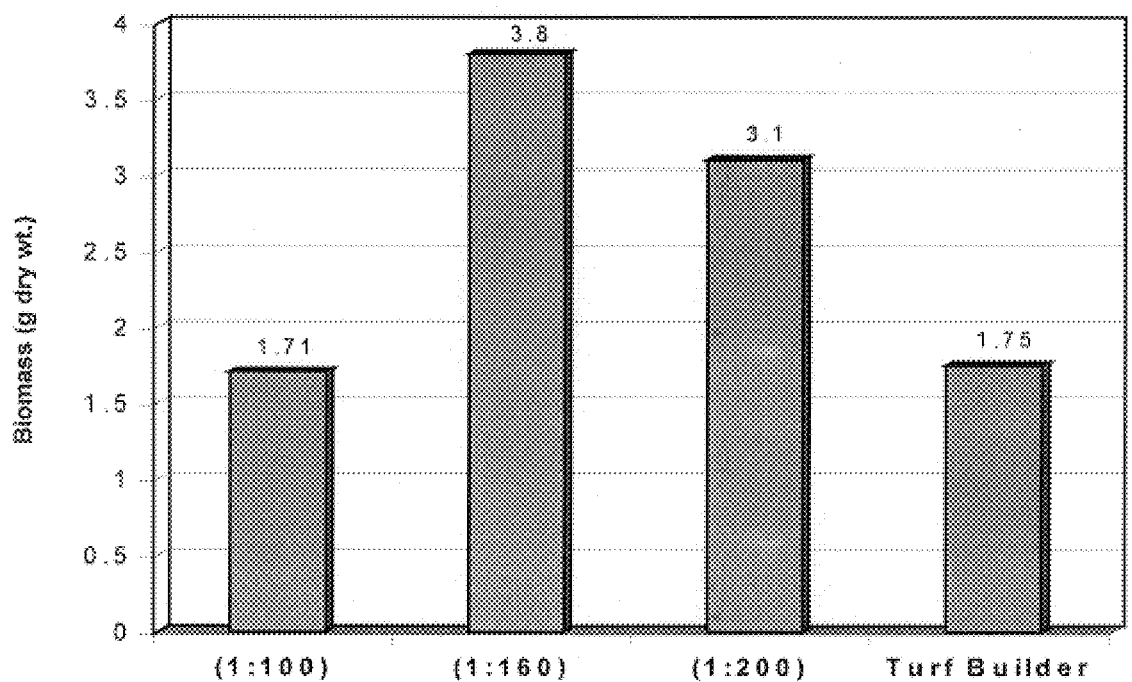
Fig. 5a. Turf Roots (pots) - Dry Weight
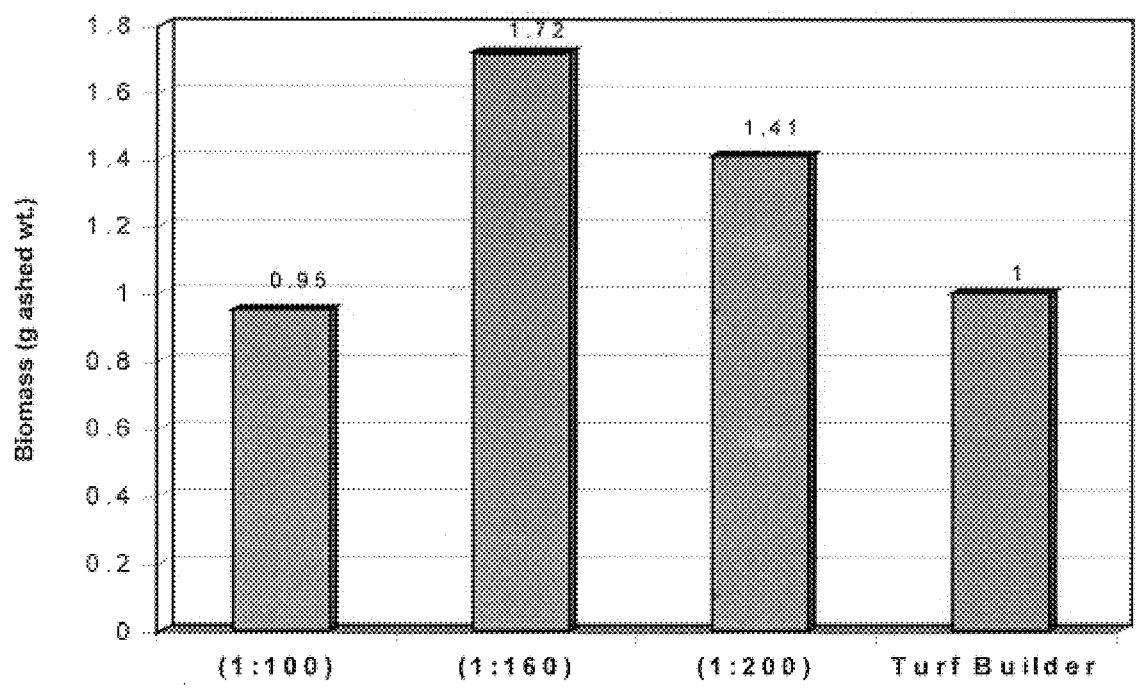
Fig. 5b. Turf Roots (pots) - Ashed Weight

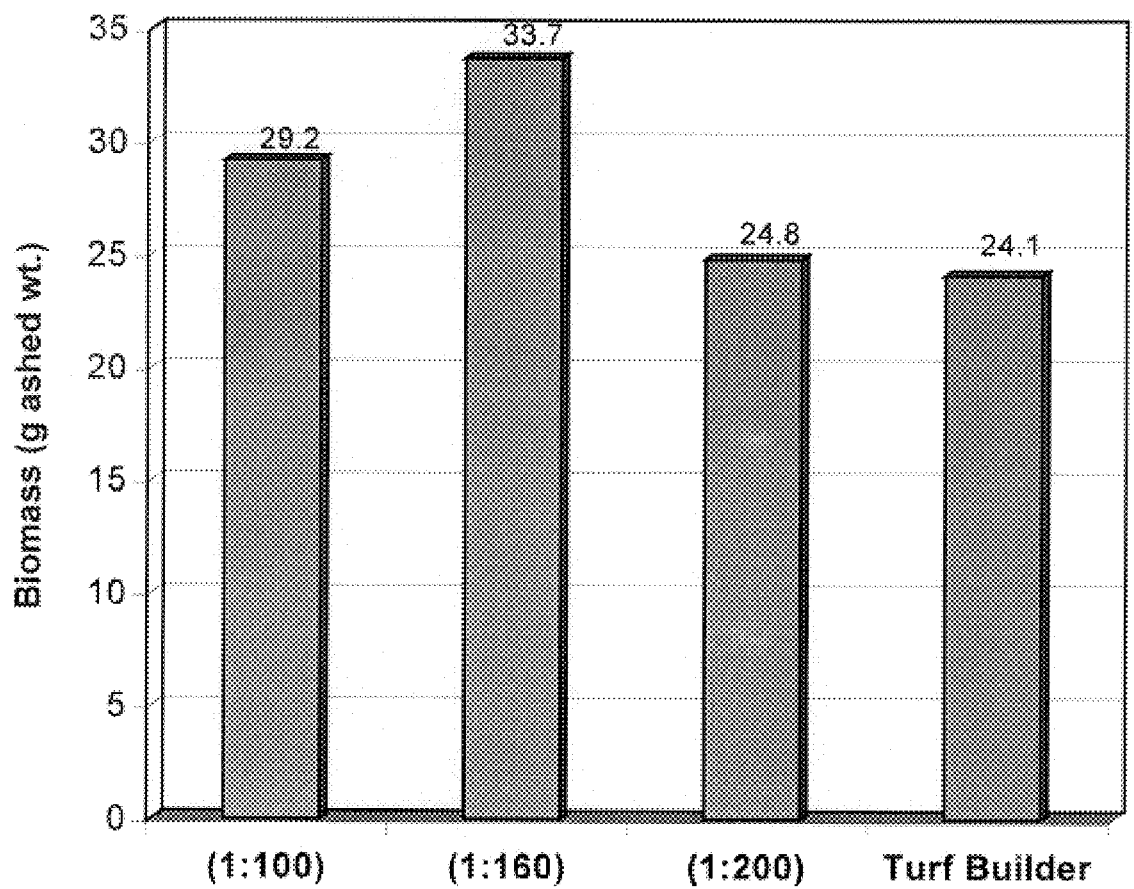

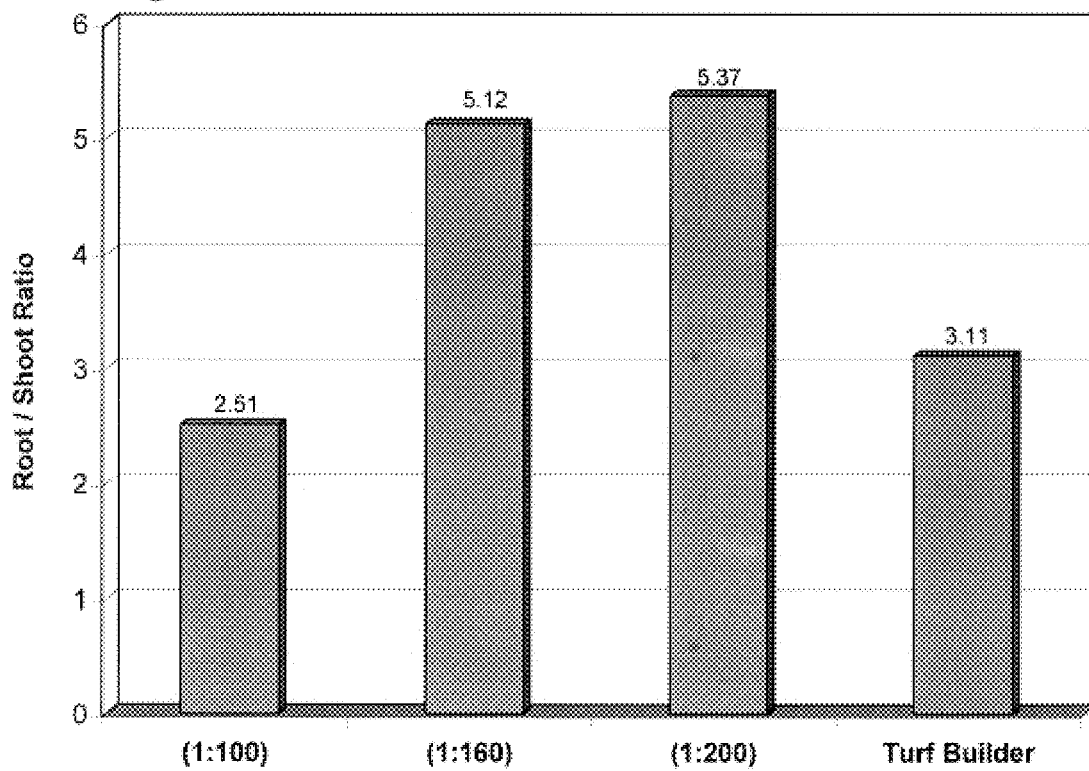
Fig. 6a. Turf Root/Shoot Ratio
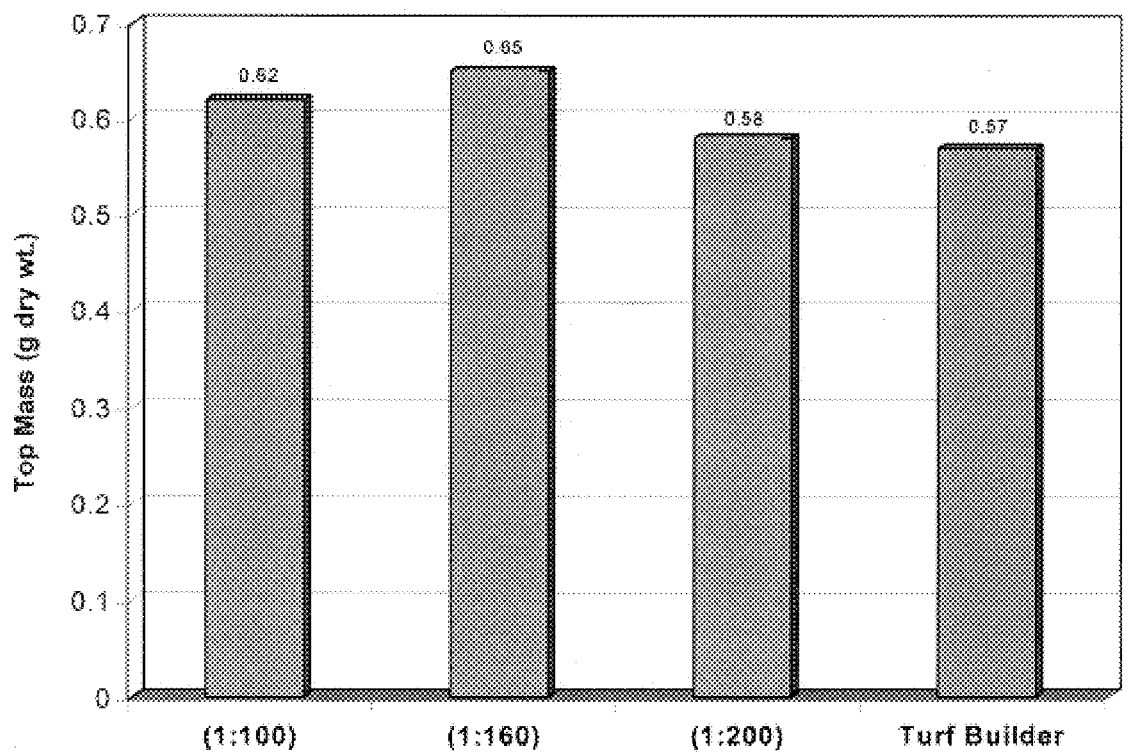
Fig. 6b. Turf Top Mass

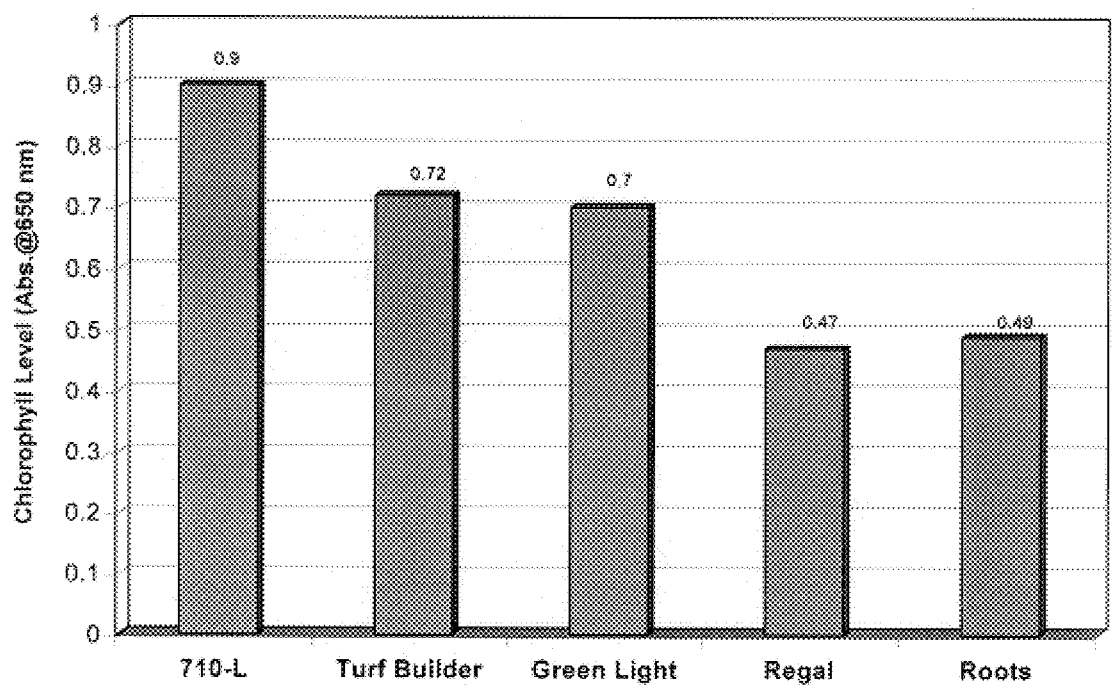
Fig. 7. Turf Chlorophyll Content

NUTRIENT PLANT FORMULATION WITH MICROBIAL STRAINS

FIELD OF THE INVENTION

This invention relates generally to a formulation for promoting plant growth and health, and more specifically to a liquid formulation which contains a novel blend of Bacillus strains and nutrients.

BACKGROUND OF THE INVENTION

Traditionally, a high level of inorganic fertilizers have been added to turf, vegetables, ornamentals and row crops to improve their growth or yield potential. Often this has resulted in more stress on plants under environmental stress (drought, physical damage) and greater susceptibility to disease. Moreover, the majority of fertilizer components, particularly nitrogen, is not utilized by the intended plants, and is lost by leaching or conversion to less desirable forms (nitrate and nitrite). Excessive leaching is now recognized as a major contributing factor to algae blooms (with subsequent pollution and loss of fish and other wildlife).

It has been recognized that plants seek to function in a mutually beneficial (symbiotic) relationship with the natural microbial strains present in soil. Indeed, as much as 25% of the total food (carbonaceous material) produced by a plant during seasonal growth is release from the roots, very likely to feed and maintain beneficial soil microbes. In turn, these microorganisms, both bacteria and certain beneficial fungi (i.e. mychorrhizae) provide the plant with specific metabolites and micronutrients that significantly aid overall plant health and development.

Certain of these microbial metabolites have been identified as precursors to natural phytohormones which plants synthesize and use at key times in their growth cycle, or during times of stress and infection. Some of these precursors, referred to as plant growth regulators (PGR), have been applied directly to plants to encourage growth at desired times. However, we have realized that some bacteria produce specific natural phytohormone precursors (e.g. indole-3-ethanol; TOL) and are well-adapted to grow on (colonize) plant roots. These strains subsequently provide the plant with these metabolites in a way far better than relying on exogenous application of the synthetic chemical precursors alone. This is due to the fact that root-colonizing beneficial bacteria respond in a feedback relationship to the overall levels of plant root exudate, growing and producing more phytohormone precursors at just the right times and amounts for the plants to use the material most effectively. From beneficial strains, these precursors are usually non-toxic, readily available (taken up by the roots) and can be stored by the plant for future rapid response at key times of development or stress.

Other microbial strains have been isolated which demonstrate the ability to produce several anti-fungal metabolites. These natural antibiotics specifically deter the development of pathogenic plant fungal organisms. These strains, which also produce TOL, have been included in the formulation described, to provide a further natural (non-chemical) assistance to the plant in resisting common disease-causing fungi. Another microbial organism (*Paenibacillus azotofixans*) isolated from grass roots for its ability to fix atmospheric nitrogen into plant-usable substrates, was also included in the formulation to augment available nutrients in the immediate root area.

Importantly, it has been determined that the optimal benefits are achieved through a combination of such selected phytohormone (precursor) producing soil bacteria, antibiotic producing strains, and free-living nitrogen-fixing isolates, along with certain nutrients and micronutrients in specific empirically-determined levels. Such a formula provides surprisingly effective conditions to achieve optimal plant vigor and stress tolerance for a relatively broad array of agronomically important plants and crops. In the past, other products have been developed and sold which included some of these elements separately, such as PGR-containing solutions (e.g. Regal®), beneficial microbial strains alone (e.g. Dagger-G®); standard inorganic fertilizers (e.g. Miracle Gro®, Turf Builder®). We have found by direct comparison on a variety of plant types that the unique combination of the selected bacterial strains, phytohormone-precursors, and nutrients is far more effective in improving plant vigor and final yield potential.

SUMMARY OF THE INVENTION

The present invention is directed to a novel liquid formulation which enhances plant growth and provides resistance to fungus and other common plant diseases. The invention utilizes a novel blend of a plurality of bacillus strains which in combination with a blend of selected nutrients and micronutrients provides a unique synergism in the enhancement of plant growth and health.

There are several ways by which the liquid formulation of the present invention, hereinafter designated 710-L, is acting to potentiate growth, including: i) Microbial input of non-toxic phytohormones (e.g. indole-3-ethanol; TOL); ii) Inhibition of deleterious fungal organisms through the production or anti-fungal antibiotics (e.g. zwittermicin; kumamycin) and hydrolytic enzymes (e.g. xylanase; cellulase; protease; chitinase); iii) Nitrogen fixation by free-living, root-associated bacteria (e.g. *Paenibacillus azotofixans*); iv) Synergy of plant beneficial microorganisms with nutrients and micronutrients, particularly low levels of purified phytohormones and phytohormone precursors. The patent describes the unique combination of these modes of action to provide a complementary, and occasionally synergistic benefit for plant growth, particularly under higher stress conditions such a nutrient deficiency, low moisture, and physical damage.

Microbial-produced Phytohormones

The body of evidence is strong that specific microbial-produced phytohormones are taken up and stored by the plant, and are later used at key times in plant development for more efficient nutrient utilization and stress tolerance. In particular, indole-3-ethanol (TOL; tryptophenol) and indole-3-acetic acid production by root-associated bacterial strains are believed to be especially beneficial to plant growth promotion See the literature as evidenced by: Lebuhn, M., Heulin, T., and Hartmann, A. (1997) Production of auxin and other indolic and phenolic compounds by *Paenibacillus polymyxa* strains isolated from different proximity to plant roots. FEMS Microbiology Ecology 22: 325–334.), Sandberg, G. (1984). Biosynthesis and metabolism of indole-3-ethanol and indole-3-acetic acid by *Pinus sylvestirs L.* needles. Planta 161:398–403.), Lebuhn, M, and Hartmann, A. (1996) Indolic and phenolic compounds. Auxins, L-tryptophan and related indolic and phenolic catabolites. In: *Methods in Soil Biology* (Schinner, F. Ohlinger, R., Kandeler, E. and Margesin, R., Eds.), Springer-Verlag, Berlin, pp. 266–280), Martin, P., Glatzle, A., Kolb, W., Omay, H., Schmidt, W. (1989) N2-fixing bacteria in the rhizosphere: Quantification and hormonal effects on root development. Z Pflanzenemaehr Bodenkd 152: 237–245.), and Muller, M., Deigele, C., Ziegler, H. (1989) Hormonal interactions in the rhizosphere of maize (*Zea mays L.*) and their effects on plant development. Z Pflanzenernaehr Bodenkd 152: 247–254.) The lipolytic nature of TOL allows for rapid root uptake and efficient storage without concomitant toxicity often associated with indole acetic acid (IAA; See Sandberg publication above). Many of the strains in the BiChem® 710-L and BiChem® 710-GN have been selected for, or found capable of producing TOL as well as other indole-like derivatives. This was demonstrated as described in Example IV, below. Strains that produce IAA itself have been purposefully excluded from the formulation largely due to the association of IAA with plant-pathogenic bacteria, and potential deleterious effects on plant development. (See Brandl, M. T., and Lindow, S. E. (1998) Contribution of indole-3-acetic acid production to the epiphytic fitness of *Erwinia herbicola*. Appl. Env. Mirobiol. 64:3256–3263).

Inhibition of Deleterious Fungi

Soil-borne and foliar pathogenic fungi provide a strong challenge to growing plants, particularly early in development and under stressed conditions (See Cook, R. J. (1980) Fusarium foot rot of wheat and its control in the Pacific Northwest. Plant Desease 64: 1061–1066. Cook, R. J., and Naiki, T. (1982) Virulence of Gaeumannomyces graminis var. tritici from fields under short-term and long-term wheat cultivation in the Pacific Northwest. Plant Pathology 31:201–207. In addition, significant evidence exists that a number of non-pathogenic but deleterious soil fungi also play a role in depressing the full potential of plant establishment and growth. (See Schroth, M. N., and Hancock, J. G. (1982) Disease-suppressive soil and root-colonizing bacteria. Science 216: 1376–1381). The ability of certain plant growth-promoting rhizobacteria (PGPR) to inhibit the establishment of disease fungi or to act against deleterious organisms has been well established as described in: Schroth, M. N., Loper J. E., and Hildebrand, D. C. (1984) Bacterial as biocontrol agent of plant disease. In: *Current Perspectives in Microbial Ecology* (M. J. Klug and C. A. Reddy, eds.), Am. Soc. for Microbiol., Washington, D.C., pp. 361–369). and Lambert, B., and Joos, H. (1989) Fundamental aspects of rhizobacterial plant growth promotion research. Trends Biotechnol. 7:215–219). Several novel anti-fungal agents produced by soil microorganisms have been isolated, including zwittermicin and kanosamine, which are effective against a broad range of pathogenic and deleterious fungal species (Silo-Suh, L. A., Stabb, E. V., Raffel, S. J., and Handelsman, J. (1998) Target Range of Zwittermicin A, an amionpolyol antibiotic from Bacillus cereus. In: Current Microbiology Vol. 37, Springer-Verlag, New York, pp. 6–11. One of these strains, Soy 130 is present 710-L and 710-L GN (dry) formulae. Certain soil bacteria (Paenibacillus and Bacillus species) are capable of producing several hydrolytic and fungal cell wall-degrading enzymes, such as cellulase, mannanase, xylanase, chitinase, and proteases, as well as enzymes (e.g. trehalase) which decrease fungal osmotolerance. Note: Nielsen, P., Sorensen, J. (1997) Multi-target and medium-independent fungal antagonism by hydrolytic enzymes in *Paenibacillus polymyxa* and *Bacillus pumilus* strains from barley rhizosphere. FEMS Microbiol. Ecology 22:183–192). and Sakai, K., Yokota, A., Kurokawa, H., Wakayama, M., and Moriguchi, M. (1998) Purification and characterization of three thermostable endochitinases of a noble Bacillus strain, MH-1, isolated from chitin-containing compost. Appl. Env. Microbiol. 64:3397–3402). and Gaballa, A., Abeysinghe, P. D.,Urich, G., Matthijs, S., DeGreve, H., Cornelis, P., and Koedam, N. (1998) Trehalose induces antagonism towards *Pythium debaryanum* in *Pseudomonas fluorescens* ATCC17400.) At least two strains present in the 710-L formulae SB3002 and SB3054, are among these classes of bacteria, and are capable of producing such inhibition factors.

Nitrogen Fixation by Free-living, Root-associated Bacteria

Nonsymbiotic nitrogen fixation by plant-associated bacteria is believed to provide a significant contribution to the overall nitrogen gain under certain conditions (Seldin, L, Van Elsas, J. D., and Penido, E. G. C. (1983) Bacillus nitrogen fixers from Brazilian soils. Plant and Soil 70:243–255. The increasing use of low-input sustainable agriculture (LISA) for major crops, and the expansion of golf-course greens on high sand/peat bases are creating significant challenges in nitrogen availability. The soil organism *Paenibacillus azotofixans* has been identified as such a free-living nitrogen-fixing bacterial species, and such a strain (SB3054) is present in the 710-L formulae. Note: Seldin, L, Van Elsas, J. D., and Penido, E. G. C. (1984) *Bacillus azotofixans* sp. nov., a nitrogen-fixing species from Brazilian soils and grass roots. International Journal of Systemic Bacteriology 34:451–456).

Synergy of Plant Beneficial Microorganisms with Nutrients and Micronutrients

Soil bacteria, by providing key storage phytohormones, inhibiting deleterious and pathogenic fungi, and enhancing the available nitrogen pool, allow the plant to reach its optimal potential for growth, vigor and yield. It has been found that the effect of the fully formulated 710-L material provides more than the additive beneficial growth effect of either base formula (all but the bacterial strains) or the microbial strains alone. This is conceptually reasonable, since an improvement in root mass and even the stimulation of beneficial mychorrhizae fungi has been demonstrated as directly attributable to certain phytohormones such as those produced naturally by soil microbes (indole butyric acid and IAA) as described by: Arshad, M., and Frankenberger, W. T. Jr. (1998). Plant growth-regulating substances in the rhizosphere: Microbial production and functions. In: *Advances in Agronomy Vol.* 62, Academic Press, New York. pp. 45–151. It has been found that by adding a very low levels ($10^{-7}$ to $10^{-8}$ molar) of indole butyric acid (IBA) and the phytohormone precursor tryptophan (trp), roots appear to be initially stimulated to provide increased exudate and a greater surface area. This would lead to the more rapid and extensive colonization by the added bacterial strains in the product. This combination of root potentiation and enhanced colonization is a unique feature of this product, with immediate and long-range benefit to plant development, vigor, and stress tolerance.

The formulation has been shown to enhance plant growth in a wide variety of vegetables and ornamental plants. Due to the novel combination of bacillus strains and nutrients, the formulation of the invention provides an economical and effective alternative to conventional "fertilizer" intensive growing systems.

BRIEF DESCRIPTION OF THE DRAWING

For a fuller understanding of the nature and objects of the invention, reference should be made to the following detailed description of a preferred mode of practicing the invention, read in connection with the accompanying drawings, in which:

FIG. 1 illustrates a graphic plot of the results of turf growth chamber trials.

FIG. 2 illustrates a graphic plot of the results of turf field trials.

FIGS. 3*a*–3*d* illustrate a graphic plot of the results of a greenhouse test.

FIGS. 4a–4d illustrate a graphic plot of the results of a second greenhouse test.

FIGS. 5a–5c illustrate a graphic plot of the results of a third greenhouse test.

FIGS. 6a and 6b illustrate a graphic plot of additional results from the third greenhouse test.

FIG. 7 illustrate a graphic plot of the results of a turf chlorophyll test.

DETAILED DESCRIPTION OF THE INVENTION

The formulation of the present invention has a unique combination of a plurality of bacillus strains and nutrients. One or more of the bacillus strains provides for the production of a non-toxic phytohormone which enhances plant growth. Other bacillus strains contribute to plant growth in other ways such as through nitrogen fixation. Still others contribute to plant health such as by providing an antifungal effect.

The formulation further includes a blend of nutrients and micronutrients which enhance microbial activity and plant growth and health. The formulation also includes a phytohormone component, and a phytohormone precursor. The bacillus strains are present in a range from about $4 \times 10^6$ to $4 \times 10^9$ CFU/ml.

The following tables illustrate one embodiment of a preferred formulation of the present invention, with the specific breakdown of the micronutrient formulation being presented in Table 2. Formulation is based on a 100-fold concentrate.

TABLE I

PRODUCT FORMULATION (710L)

| Bacillus Strain | ATCC Number | Target Count* | Range* |
|---|---|---|---|
| DA-33 | ATCC 55406 | $2.04 \times 10^7$ | $1 \times 10^6$–$1 \times 10^9$ |
| SB3002 | ATCC 700385 | $2.125 \times 10^7$ | $1 \times 10^6$–$1 \times 10^9$ |
| SB3003 | ATCC 700386 | $2.125 \times 10^7$ | $1 \times 10^6$–$1 \times 10^9$ |
| Soy130 | ATCC 202076 | $2.125 \times 10^7$ | $1 \times 10^6$–$1 \times 10^9$ |
| P. azotofixans | ATCC 35681 | $0.085 \times 10^7$ | $1 \times 10^5$–$1 \times 10^9$ |

| Nutrient | LBS/GAL | Range |
|---|---|---|
| Diammonium Phosphate | 0.236 | 0.1–0.5 |
| Potassium Nitrate | 0.0187 | 0.002–0.2 |
| Urea N Source | 0.136 | 0.01–1.5 |
| Monopotassium Phosphate | 0.17 | 0.01–1.0 |
| Potassium Bicarbonate | 0.228 | 0.05–0.50 |
| Micronutrients (Table 2) | 0.417 | 0.02–4.0 |
| Kathon CG/ICP | 0.00333 | 0.0003–0.03 |
| Mint Green Dye | 0.0000834 | 0.000008–0.008 |

| Test | Specification | Range |
|---|---|---|
| Spore Count | $\geq 5.0 \times 10^{7*}$ | $4 \times 10^6$–$5 \times 10^{9*}$ |
| pH | 7.5–8.5 | 6.0–9.0 |
| MacConkey | Negative | — |

*Units are CFU/ml.

TABLE 2

MICRONUTRIENT FORMULATION FOR 275 GALLONS

| INGREDIENT | Pounds Required | Range |
|---|---|---|
| City Water | 2294 | |
| Potassium Chloride KCl | 109.8 | 5 300 |
| Hampene (Chelated Iron) | 4.82 | 0.2 50 |
| Disodium dihydro molybdate $Na_2MoO_4.2H_2O$ | 0.11 | 0.01–0.4 |
| Cobalt chloride hexahydrate $CoCl_2.6H_2O$ | 0.00459 | 0.001–0.01 |
| Nickel chloride hexahydrate $NiCl_2.6H_2O$ | 0.00459 | 0.001–0.01 |
| IBA (Indole-3-butryic acid) | 0.44 | 0.02–4.0 |
| L-tryptophan | 0.184 | 0.02–2.0 |

The following dry formulation (710-GN; Tables 3 and 4) represents a further embodiment of the present invention.

TABLE 3

710-GN FORMULATION
Lbs. of Ingredient per 100 Lbs. of Product

| INGREDIENT | CODE | TARGET |
|---|---|---|
| DA33 Intermediate | 9009 | 2.14 |
| SB3002 Intermediate | 9210 | 4.33 |
| SB3003 Intermediate | 9212 | 8.67 |
| Soy 130 Intermediate | 9451 | 34.67 |
| P.azotofixans Intermediate | 9452 | 0.22 |
| Corn Gluten | 161 | 41.2 |
| Diammonium Phosphate | 109 | 1.18 |
| Potassium nitrate | 276 | 0.093 |
| Urea | 395 | 0.679 |
| Monopotassium Phosphate | 241 | 0.848 |
| Potassium bicarbonate | 273 | 1.142 |
| Micro AG Dry (Table 4) | 9458 | 0.236 |

TABLE 4

Micro AG Dry FORMULATION FOR 100 Lbs.

| INGREDIENT | Pounds Required | Range |
|---|---|---|
| Potassium Chloride KCl | 95.155 | 5–180 |
| Hampene (Chelated Iron) | 4.201 | 0.2–50 |
| Disodium dihydro molybdate $Na_2MoO_4.2H_2O$ | 0.096 | 0.01–0.4 |
| Cobalt chloride hexahydrate $CoCl_2.6H_2O$ | 0.004 | 0.001–0.01 |
| Nickel chloride hexahydrate $NiCl_2.6H_2O$ | 0.004 | 0.001–0.01 |
| IBA (Indole-3-butryic acid) | 0.38 | 0.02–4.0 |
| L-tryptophan | 0.16 | 0.02–2.0 |

SPECIFICATION

| TOTAL SPORE COUNT | $\geq 2.0 \times 10^{9*}$ |
|---|---|
| TOTAL GRAM NEGATIVE COUNT | $\geq 0.15 \times 10^{9*}$ |
| TOTAL BACTERIAL COUNT | $\geq 2.15 \times 10^{9*}$ |

*Units are CFU/ml.

The following field testing and comparative testing was conducted using formulations of the present invention.

I. Turf Growth Chamber Trials

Summary

This growth Chamber Trial measured the top mass growth-promoting effects of 710-L on turf (Scotts® Sun and Shade fairway mix). The study included separate treatments of 710-L, strains only (five Gram-positive spore types, including *P. azotofixans* SB3054 and Soy130), Turf Builder® (at recommended rate of 15 lbs/5000 sq. ft.), 710-L base (nutrients only) and water.

Pot Preparation

A sand:peat mix (80:20) was prepared according to USGA specifications and added to 4" diameter pots. Grass seed (Scotts Sun and Shade Fairway mix; 0.5 g) was evenly distributed over the surface of each pot. The pots were covered with a wide screen mesh to aid in germination and to facilitate even grass trimming.

Each pot was watered initially with 150 ml of a dilute nutrient solution to insure even germination (Miracle Gro: ¼ teaspoon/gallon). Pots were kept under grow lights in a temperature controlled chamber through the course of the experiment.

Treatment

After germination was evident (first grass leaves visible), the following treatments were applied on a weekly basis. In this treatment the 710-L formulation did not contain the phytohormones (IBA & TRP) in the micronutrients:

710-L 1:100 dilution; 50 ml per pot

710-L (base) 1:100 dilution; 50 ml per pot

Water 50 ml per pot

Turf Builder 1.4 g/pot of a 1:10 blend of Turf Builder:sand

Pots were watered as needed from below to maintain adequate moisture levels uniformly. The experiment continued for 8 weeks. Grass was maintained at an even height for all treatments, and clippings were collected, dried and weighed.

Results

Results shown in FIG. 1 indicate that 710-L performed similar to Turf Builder® in maintaining turf top mass, even though inorganic nitrogen addition from 710-L was less than 25% that provided by Turf Builder®.

Amount N applied per pot:

Turf Builder=30 mg/pot (standard rate)

710-L=7 mg/pot (1:100 dilution rate)

710-L treatment was much better than strains alone, 710-L base (no strains) and the water control.

As can be seen from the data in this example, 710-L with the microorganisms present provides a strong plant-beneficial effect even when the total nitrogen (N) addition is at 1.44 lbs N/1000 ft$^2$ after 8 weekly treatments. This is significantly less than the 6.16 lbs N/1000 ft$^2$ provided by the standard rate of Turf Builder®, or equivalent inorganic fertilizers commonly used by those skilled in the art. The phytohormone-producing microorganisms in 710-L appear to potentiate the plant roots to more efficiently gain nitrogen and other nutrients from the soil. Since nitrogen application rates often average 5–10 lbs N/1000 ft$^2$ on golf course greens during the active growing season, 710-L treatment offers both a more cost-effective means to maintain plant vigor and a more environmentally responsible means to deliver adequate nitrogen to the plant. By adding less nitrogen, low soil pH is more readily avoided with less nitrous acid build up, leading to higher plant metabolic activity with less lime application required (often added to raise pH). Moreover, less nitrate (fertilizer) addition lowers the negative impact potential of this compound on groundwater quality and lagoon algae development.

Similarly, other primary nutrients in 710-L, including phosphorus (P) and potassium (K) are added at a relatively low levels compared with standard inorganic fertilizer recommendations. As can be derived from Table I, ten bi-weekly applications of the recommended rate of 710-L (on turf) at 18 oz/1000 ft$^2$ provides total seasonal levels of nitrogen, phosphorus, and potassium of only 0.17 lbs N/1000 ft$^2$, 0.13 lbs P/1000 ft$^2$, and 0.22 lbs K/1000 ft$^2$, respectively. While 710-L is not recommended as a fertilizer per se, inclusion of the 710-L formulation in a balanced fertilization program can permit a significant (20–50%) reduction in total inorganic nutrient application, while enhancing overall plant development, appearance, and vigor.

II. Turf Field Trials 1997: Hollyfield Golf Course

The field turf trials are designed to address the following issues:

1) Whether the 710-L turf formula without SB3054, IBA and TRP (no surfactant) will continue to stimulate strong turf root development and overall plant vigor.

2) Whether the *P. azotofixans* strain (SB3054) can improve performance based on its natural nitrogen fixation ability.

3) Whether the microbial strains alone are capable of stimulating vigor.

Also, a commercial organic nutrient formulation (GR) was assessed with and without additional microbial strains.

Treatment Summary

Four treatments were applied as well as an untreated control:

1) 710 (includes four bacterial strains: DA33, SB3002, SB3002, Soy130 but not *P. azotofixans*)

2) 710-L Base (no strains)

710-L with five bacterial strains (as in Treatment #1) plus *P. azotofixans*

4) Bacterial strains only (five strains)

5) Untreated control

Two additional treatments (organic fertilizer):

6) GR plasma+Five bacterial strains

7) GR plasma alone

Test Procedures

The test parameters and application rates include:

Plot Arrangement:

10 ft×8 ft test plots, with 3 ft buffer zones between each plot

Application schedule:

1) 1 gallon of 2× dilution on each 80 ft$^2$ test plot (Day 1) Dilution: ~300 ml 710-L/gallon sprayed 2) 1 gallon of 1× dilution on each 80 ft$^2$ test plot (Day 14) Dilution: ~150 ml 710-L/gallon sprayed 3) 1 gallon of 1× dilution on each 80 ft$^2$ test plot (Day 28) Dilution: ~150 ml 710/gallon sprayed All treatments were watered-in with sprinkler hose (45–60 min)

This application rate gives an overall nitrogen (N) delivery of 0.235 lbs N/1000 ft$^2$. This is similar to the low rates being used on golf course greens when applying other organic fertilizers (e.g. GR), or practicing LISA (Low Input Sustainable Agriculture) methods.

Treatments timing:

One day prior to first application (Day 0), area was mowed to uniform height. Then:

Site was then photographed 5 core samples were retained per plot

Core holes left after sampling were replaced with soil/turf mix

Core samples were composited from each treatment

Analysis procedure:

Top growth was separated from roots to obtain total wet weight

Roots were washed lightly to remove loose soil

Washed roots were agitated in filtered distilled water to remove tight soil along with rhizoplane strains (bacterial root colonists)

Roots were then dried overnight and weighed

Analysis timing:

Analysis at Days 0, 21, and 42 (two weeks after final application)

All plots received their normal agronomic care, including mowing, and irrigation.

Results

Root enhancement (FIG. 2) was found greatest after treatment with 710-L (with all 5 bacterial strains, followed by 710 (4 strains without *P. azotofixans*). Poor root enhancement relative to the untreated control was achieved using either the nutrient blend (710 Base) or the natural organic formulation (GR) without microbial strains. This demonstrates that the added microbial strains play a significant role in root enhancement, and stimulation was not due solely to additional inorganic or organic nutrients present in the formulations.

III. Turf Field Trials 1998: Countryside Golf Course

A field study on an in-play golf course green tested three treatments: 710-L; 710-GN; and a blend of two other beneficial soil organisms, *Azospirillum calcoaceticus* and *Cellulomonas* sp. (referred to as "Azo/Cell") on approximately 1000 ft$^2$ of actual playing surface grass (*Poa annua*). This green had been stressed by both disease and physical conditions. 710-L and Azo/Cell were applied as a 1:25 spray on the turf surface at 3.5 gal/1000 ft$^2$, once per week for 4 weeks. 710-GN (as a dry formulation) was applied at a 10 lb/1000 ft$^2$ rate once per week for three weeks. Azo/Cell was prepared by production as a fresh culture blend with a total cell count of approximately $3\times10^9$ CFU/ml (concentrate), and applied at $6\times10^7$ CFU/ft$^2$.

Results after 10 days gave a visual indication (photographed) that 710-L most improved the color and density of the turf followed by 710-GN. There was no discemable difference between the Azo/Cell treatment and the remainder of the turf on this green. However, since this green had also been treated with a fungicide and additional nutrients, the improvements noted at 10 days were no longer evident by 3 weeks. Nevertheless, the grass from the treated areas continued to look at least as healthy as the non-treated sections.

IV. Greenhouse Testing I

A series of greenhouse studies were performed to evaluate the growth enhancement effect of 710-L on both tomatoes and turf. In this example, various levels of 710-L were applied (using different dilutions of 710-L concentrate) to optimize application rates. Included in this testing was a comparison with Miracle-Gro® for vegetables and Scott's Turf Builder for turf.

Study Designs

The overall design of the study was as follows:

Tomato

Big Boy tomato seeds were germinated in Pro-Mix® soil using 4" pots for 12 pots per treatment. Seeds were allowed to germinate before treatment began. Five seeds were planted per pot, with a total of 48 pots.

4 Treatments included:

1. 710-L at 1:100 dilution; 200 ml per pot
2. 710-L at 1:160 dilution; 200 ml per pot
3. 710-L at 1:200 dilution: 200 ml per pot
4. Miracle-Gro® ¼ teaspoon/gal; 200 ml per pot An additional four-treatment set (as above) waw included, but using "Sunshine Mix® rather then Pro-Mix®. (2 pots per treatment; 8 pots total).

All treatments were made every three days (due to rapid vegetable growth under optimal greenhouse conditions); water was added as needed to maintain 80% field moisture capacity.

At day 35 assessments were made for:

Stem height; leaf length; root mass; top mass

Turf Grass

Pencross Bent Grass was sown at recommended seed density in both 4" pots and 2.9 sq. ft. planting trays.

Four Treatments included:

1. 710-L at 1:100 dilution; 50 ml per pot, 250 ml per tray
2. 710-L at 1:160 dilution; 50 ml per pot, 250 ml per tray
3. 710-L at 1:200 dilution; 50 ml per pot, 250 ml per tray
4. Turf Builder, 0.06 grams per pot, 0.96 grams per tray Three Trays per treatment (12 trays total)

8 grams of seed per tray

Four 4" pots per treatment 0.5 grams of seed per pot

Assessments performed:

Trays and 4" pots:
Photograph in side-by-side comparison
Total top mass
Total root mass using muffle furnace; ash/final dry weight It was determined in prior greenhouse experiments that a treatment frequency for tomatoes of greater than once a week was required due to the rapid growth and development of the plants under optimal summer conditions. During such optimal growth, plants reached the same stage in less than 22 days that required 35 days in the growth chamber under artificial lights. In order to treat greenhouse-grown tomatoes the same number of times during the early maturation process as used in the growth chamber trials, a greater frequency of treatments was required (treatment every 3 days instead of every 7 days).

Results: Tomato

Results of the study on tomatoes are provided in FIGS. 3 and 4. Compared with plants treated with standard inorganic nutrients (Miracle Gro®), the results demonstrate significant improvements in top mass, stem height, leaf length and root mass for plants grown in the standard nursery soil blend Pro-Mix® BX, and improvements in top mass, stem height and leaf length for plants in Sunshine Mix®. A dilution rate of the 710-L concentrate of 1:160 is optimal for the Pro-Mix® and 1:100 is generally best for Sunshine Mix®.

Results: Turf

Turf trials were conducted in both 4" pots and in large 2'×1' trays, and compared root and shoot enhancement for three dilutions of 710-L (1:100; 1:160; and 1:200). Visually, the turf treated with 710-L exhibits more vigorous foliar density compared with standard TurfBuilder® treatment, particularly for the 1:100 and 1:160 dilutions of 710-L. FIG. 5 summarizes the turf root mass results following triplicate treatments of turf in pots for 35 days, then analyzed by both standard root washing (FIG. 5A) and by muffle furnace ashed weight (FIG. 5B). FIG. 5C provides the ashed dry weights for turf treated as in the pot test, but grown in the larger flats. Results indicate that a weekly treatment (3 total applications) with a 1:160 dilution of 710-L provides the best root/shoot ratio, significantly better than TurfBuilder® (FIG. 6a). Even at the 1:200 dilution, roots were significantly better than TurfBuilder® without an increase in top mass (FIG. 6b). This is important as it demonstrates that additional mowing would not be required when turf is treated with product.

V. Greenhouse Testing II

A second round of greenhouse trials of 710-L on ornamental plants, turf, and vegetables, treated as described in Section IV (Greenhouse Test) was completed to assess both overall plant health and chlorophyll content.

Ornamental Plants

Duplicated tests were performed comparing both *Zebrina pendula* (Wandering Jew) and *Chlorophytum comosum* (Spider Plant) treated with either 710-L (1:100) or Miracle Gro®. For these studies, identical size cuttings were propagated from a mother plant, treated weekly with product, and grown under the same conditions for 11 weeks. Propagated plants treated with 710-L exhibited dramatically better size, color, and overall health appearance than plants treated with Miracle Gro®.

Turf: Chlorophyll Production

A growth chamber study was conducted to assess the level of chlorophyll produced in turf leaves following 5 weeks of treatment with 710-L. This was compared with standard treatments of several other materials, including: Turf Builder®, Green Light®, Regal®, Roots®, and water alone.

Pot Preparation for Chlorophyll Study

A sand:peat mix (80:20) was prepared according to USGA specifications and added to 4" diameter pots. Grass seed (Pencross Bentgrass; 0.5 g) was evenly distributed over the surface of each pot. The pots were covered with a wide screen mesh to aid in germination and to facilitate even grass trimming.

Each pot was watered initially with 150 ml of a dilute nutrient solution to insure even germination (Miracle Gro: ¼ teaspoon/gallon).

Treatment

After germination was evident (first grass leaves visible), the following treatments were applied on a weekly basis:

710-L 1:100 dilution; 10 ml per pot ($\frac{1}{5}^{th}$ level described in Example I)

Green Light® 1:75 dilution; 10 ml per pot

Regal® 1:100 dilution; 10 ml per pot

Roots® 1:60 dilution; 10 ml per pot

Turf Builder® 0.14 g/pot

Water 5.0 ml additional per pot

Pots were watered as needed to maintain adequate moisture levels uniformly (80% field capacity). The experiment continued for 6 weeks. Grass was maintained at an even height for all treatments, and clippings were collected at the end of the study and analyzed for chlorophyll content. This analysis was performed by combining 1 g of wet-weight grass blades from triplicate pots of each treatment with 50 ml of acetone (Sigma-Aldrich; technical grade). This was subjected to tissue grinding for 10 sec, then filtered through a glass-fiber filtration device, collecting (but not evaporating) the chlorophyll:acetone extract. Clippings from the first extraction were collected from the glass-filtration, the extracts were combined. Spectrophotometric absorbance at 650 nm was used to assess the relative chlorophyll content of grass from all treatments.

Results

The results of the chlorophyll analysis are shown in FIG. 7. These confirm the ability of the 710-L formulation to significantly enhance the chlorophyll content (green color) of the treated plants as compared to those plants treated with standard rates of Turf Builder®, Regal®, or Roots®.

Vegetables

Further studies on vegetables have provided additional confirmation that the full 710-L formula is much more effective in growth enhancement than the same formula but without the added microbial strains (referred to as 710-L Base). This was true for all measured parameters, including stem height, leaf length, and root mass. For example, results of two trials demonstrated that the 710-L Base was 51% and 22% less than the full 710-L (with microbes) in stem height, and 43% and 8% less than 710-L in leaf length. Treatment with microbes alone had 67% lower stem heights and 68% shorter leaf lengths than plants treated with 710-L. No individual microbial strain present in the full 710-L, when added to 710-L Base, was capable of reproducing the complete benefit seen for when all strains were present together. This argues that the beneficial effect of the microbes is at least additive and perhaps synergistic. However, each of the individual strains present in the 710-L formulation was shown to provide a significant beneficial effect on plant growth (stem height and leaf length).

VI. Production of Natural Phytohormones by Selected Microorganisms

Standard TLC (Thin Layer Chromatography) was used to demonstrate the potential for bacterial strains present in BiChem® 710-L to produce either or both indole-3-ethanol (TOL) and indole acetic acid derivatives (but not IAA itself). Isolated bacterial strains were grown for 16–18 hours in sterile dilute nutrient broth containing 0.1% D-L tryptophan. Cultures were centrifuged, and 10 microliters of the culture supernatant was applied to silica gel TLC glass plates with fluorescent indicator (Sigma-Aldrich, Milwaukee, Wis.) along with 0.1 mg methanolic solutions of the phytohormone standards TOL, IAA, IBA (indole butyric acid), IPA (indole propionic acid), and MIA (indole acetate methylester). After drying applied samples, plates were developed in glacial acetic acid:cholorform [5:95] for 2 hours, and photographed under UV light (320 nm). $R_f$ values of bacterial-produced phytohormones were compared with known standards for identity. Results indicated that strains DA33, SB3002, SB3003, Soy130 and SB3054 (*P. azotofixans*) are all capable of producing TOL. Strains DA33 and Soy130 appear to also produce a derivative or precursor of IAA (possibly tryptophan), found present in the IAA standard material (Sigma-Aldrich, Milwaukee, Wis.).

VII. Field Assessment: Vegetables and Other Crops

Field studies using the 710-L formulation have demonstrated significant benefits for both plant yield (tomato, pepper, corn, soybean) as well as plant vigor and appearance (turf, ornamentals). Field treatment of tomato and pepper with 710-L gave an average yield increase of 45% over plants treated with Miracle Gro® for 8 of 11 varieties studied at four different field sites. Treatment of corn (5 acres) and soybean (5 acres) with 710-L gave average yield increases of 3.9% (corn) and 3.6% (soybean) over adjacent rows treated with the normal fertilizer regime alone.

As can be seen from the above testing, formulations of the present invention provide for enhanced plant growth and health. In addition, the comparative test data clearly shows the formulations of the present invention dramatically reduce the amount of nitrogen needed for enhanced plant growth.

While the present invention has been particularly shown and described with reference to the preferred mode as illustrated in the drawing, it will be understood by one skilled in the art that various changes in detail may be effected therein without departing from the spirit and scope of the invention as defined by the claims.

We claim:

1. A composition for enhancing plant growth, comprising:
   a formulation including Bacillus strains SB3086, SB3002, SB3003 and SB3006 having identifying characteristics of ATCC numbers 55406, 700385, 700386 and 700387, respectively.

2. The composition of claim 1, further comprising plant nutrients selected from the group consisting of diammonium phosphate, potassium nitrate, urea, monopotassium phosphate and potassium bicarbonate.

3. The composition of claim 2 further comprising plant micronutrients selected from the group consisting of potassium chloride, Hampene (Chelated Iron), disodium dihydro molybdate, cobalt chloride hexahydrate and nickel chloride hexahydrate.

4. The composition of claim 3 further comprising indole butyric acid and L-tryptophan.

5. The composition of claim 4 being in liquid or dry form.

6. The composition of claim 5, wherein the Bacillis strains are present in a range from about $1\times10^6$ to about $1\times10^9$ CFU/ml.

7. A composition for enhancing plant growth, comprising:
   (a) a formulation including Bacillus strains SB3086, SB3002, SB3003 and SB3006 having identifying characteristics of ATCC numbers 55406, 700385, 700386 and 700387, respectively, in an amount ranging from about $1\times10^6$ to about $1\times10^9$ CFU/ml;
   (b) a nontoxic amount of plant nutrients selected from the group consisting of diammonium phosphate, potassium nitrate, urea, monopotassium phosphate and potassium bicarbonate; and
   (c) a nontoxic amount of plant micronutrients selected from the group consisting of potassium chloride, Hampene (Chelated Iron), disodium dihydro molybdate, cobalt chloride hexahydrate and nickel chloride hexahydrate.

8. The composition of claim 7 further comprising indole butyric acid and L-tryptophan.

9. The composition of claim 8 being in liquid or dry form.

10. A method for enhancing plant growth which comprises, treating the plant with a formulation containing Bacillus strains SB3086, SB3002, SB3003 and SB3006 having identifying characteristics of ATCC numbers 55406, 700385, 700386 and 700387, respectively.

11. The method of claim 10 wherein said formulation further comprises plant nutrients selected from the group consisting of diammonium phosphate, potassium nitrate, urea, monopotassium phosphate and potassium bicarbonate.

12. The method of claim 11 wherein said formulation further comprises plant micronutrients selected from the group consisting of potassium chloride, Hampene (Chelated Iron), disodium dihydro molybdate, cobalt chloride hexahydrate and nickel chloride hexahydrate.

13. The method of claim 12 wherein said formulation further comprises indole butyric acid and L-tryptophan.

14. The method of claim 13 wherein said formulation is in liquid or dry form.

15. The method of claim 14, wherein the Bacillus strains are present in a range from about $1\times10^6$ to about $1\times10^9$ CFU/ml.

* * * * *